(12) United States Patent  
Sugai

(10) Patent No.: US 7,750,822 B2  
(45) Date of Patent: Jul. 6, 2010

(54) BIOMETRIC INFORMATION TRANSMITTER

(75) Inventor: Yoshinori Sugai, Chiba (JP)

(73) Assignee: Seiko Instruments Inc. (JP)

( * ) Notice: Subject to any disclaimer, the term of this patent is extended or adjusted under 35 U.S.C. 154(b) by 823 days.

(21) Appl. No.: 11/607,277

(22) Filed: Nov. 30, 2006

(65) Prior Publication Data

US 2007/0146161 A1 Jun. 28, 2007

(30) Foreign Application Priority Data

Dec. 19, 2005 (JP) ............................. 2005-364664

(51) Int. Cl.
*G08C 19/04* (2006.01)
(52) U.S. Cl. .............................. 340/870.39; 455/127.1; 455/127.5; 455/573; 702/63; 600/485; 600/500; 600/508
(58) Field of Classification Search ............ 340/870.39; 455/127.1, 127.5, 573, 572; 702/63; 600/485, 600/500, 502, 508, 509
See application file for complete search history.

(56) References Cited

U.S. PATENT DOCUMENTS 4,912,774 A * 3/1990 Saito ........................ 455/117

7,496,386 B2 * 2/2009 Liu et al. .................... 455/573
7,498,953 B2 * 3/2009 Salser et al. ........... 340/870.02

FOREIGN PATENT DOCUMENTS

JP 5317278 12/1993
JP 2002148369 5/2002

* cited by examiner

*Primary Examiner*—Albert K Wong
(74) *Attorney, Agent, or Firm*—Adams & Wilks

(57) ABSTRACT

To restrain a communicatable distance from being shortened even when a power source voltage is lowered. A heart beat signal transmission control portion controls a resonance starting oscillation portion to output a start signal in synchronism with a heart beat signal detected by a heart beat signal detecting portion and controls a resonance starting portion to output a biometric information signal in response to the start signal. An element switching portion receives a signal representing a voltage supplied from a battery portion from a voltage detecting portion and instructs the resonance starting oscillation portion to set the start signal to a period in correspondence therewith. The resonance starting oscillation portion outputs the start signal by a period in correspondence with instruction of the element switching portion. The resonance starting portion and an antenna resonance portion carry out self-excited oscillation operation in response to each start signal and transmit the biometric information signal in correspondence with the biometric signal by high power even when a power source is lowered.

5 Claims, 8 Drawing Sheets

3 WAVES
WAVEFORM

2 WAVES
WAVEFORM

BIOMETRIC INFORMATION TRANSMITTER

BACKGROUND OF THE INVENTION

1. Field of the Invention

The present invention relates to a biometric information transmitter for detecting and transmitting a biometric signal of heart beat or the like.

2. Description of the Prior Art

In a background art, there has been developed a biometric information measuring apparatus for measuring biometric information of a person of heart beat, pulse, a number of steps or the like.

For example, as a hear beat meter constituting a kind of a biometric information measuring apparatus, there has been developed a heart beat meter for mounting a biometric information transmitter for detecting a heart beat signal constituting a biometric signal and transmitting a corresponding biometric information signal by wireless to the chest of a user by a chest belt in a state of being brought into press contact therewith, receiving the biometric information by a biometric information receiver in a shape of a wristwatch and displaying the heart beat value.

There is a system of transmitting biometric information in a biometric information transmitter for measuring, processing and transmitting a heart beat signal on a side of the biometric information transmitter, or outputting a corresponding biometric information signal in accordance with the heart beat signal (refer to, for example, JP-A-2002-148369 and JP-A-5-317278).

In both of the systems, it is general to transmit the signal by modulating the signal on a carrier wave normally in order to alleviate an influence of noise from outside, however, according to the former system, an operating processing is carried out on the side of the transmitter and therefore, the latter system is preferable from a view point of simplifying a constitution on the side of the transmitter or the like.

However, also in the latter system, a battery is used exclusively as a power source and therefore, a reduction in power consumption becomes important.

According to the transmitter of the background art, when the carrier wave is outputted in accordance with the heart beat signal, a reduction in power is carried out by utilizing self-excited oscillation. Thereby, a reduction in the power consumption can be carried out.

However, in the self-excited oscillation, a signal level is attenuated in a short period of time and therefore, there poses a problem that when a power source voltage is lowered in accordance with consumption of the battery, a communication distance becomes extremely small.

The invention has been carried out in order to resolve the above-described problem and it is a problem thereof to restrain a communicatable distance from being shortened even when a power source voltage is lowered, in a biometric information transmitter.

SUMMARY OF THE INVENTION

According to the invention, there is provided a biometric information transmitter characterized in including biometric signal detecting means for detecting a biometric signal, outputting means for outputting a biometric information signal in correspondence with the biometric signal detected by the biometric signal detecting means, controlling means for controlling a transmission output of the outputting means, power source means for supplying a drive power to at least the outputting means, and power source detecting means for detecting a voltage of a power source supplied from the power source means and outputting a corresponding power source detecting signal, wherein the controlling means controls the transmission output of the outputting means in accordance with the power source detecting signal from the power source detecting means.

The controlling means controls an output power of the outputting means in accordance with the power source detecting signal from the power source detecting means.

Here, there may be constructed a constitution in which the outputting means includes self-excited oscillation means for generating the biometric information signal in correspondence with the biometric signal, wherein the controlling means controls the transmission output of the outputting means by controlling a drive timing output power of the self-excited oscillation means in accordance with the power source detecting signal from the power source detecting means.

Further, there may be constructed a constitution in which the controlling means controls the transmission output of the outputting means by controlling an output power of the self-excited oscillation means in accordance with the power source detecting signal from the power source detecting means.

Further, there may be constructed a constitution in which the controlling means shortens a period of driving the self-excited oscillation means to a predetermined value when the power source voltage supplied from the power source means to the outputting means is equal to or lower than a predetermined voltage.

Further, there may be constructed a constitution in which a center processing unit and storing means stored with a program is included, wherein the center processing unit functions as the controlling means by executing the program.

Further, there may be constructed a constitution in which the biometric signal detecting means detects heart beat, pulse or a number of steps as the biometric signal, wherein the controlling means controls the outputting means to output the biometric information at every time of detecting the biometric signal by the biometric signal detecting means.

BRIEF DESCRIPTION OF THE SEVERAL VIEWS OF THE DRAWINGS

A preferred form of the present invention is illustrated in the accompanying drawings in which.

DETAILED DESCRIPTION OF THE PREFERRED EMBODIMENTS

An explanation will be given of a biometric information transmitter according to embodiments of the invention as follows. Further, an explanation will be given of the respective embodiments by taking an example of a transmitter for a heart beat meter as a biometric information transmitter.

Figure 1:
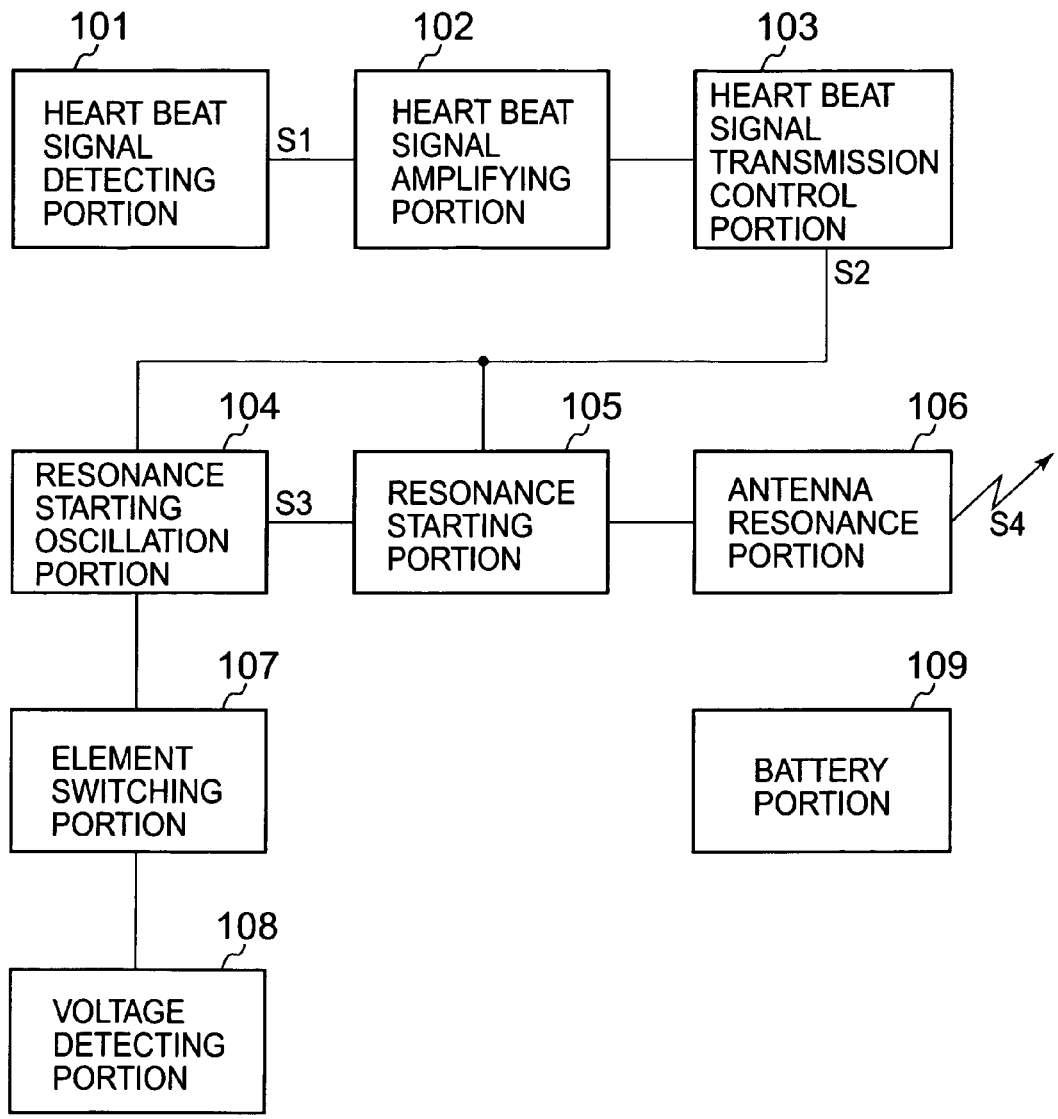
FIG. 1 is a block diagram of a biometric information transmitter according to a first embodiment of the invention.

FIG. 1 is a block diagram of a biometric information transmitter according to a first embodiment of the invention.

In FIG. 1, a transmitter for a heart beat meter includes a heart beat signal detecting portion 101 for detecting and outputting a heart beat signal of a measured person, a heart beat signal amplifying portion 102 for amplifying to output the hear beat signal from the heart beat signal detecting portion 101, a heart beat signal transmission control portion 103 for controlling transmission of the heart beat signal, a resonance starting oscillation portion 104 for outputting a start signal in response to a control signal from the heart beat signal transmission control portion 103, a resonance starting portion 105 and an antenna resonance portion 106 for carrying out a self-excited oscillation operation in response to the start signal from the resonance starting oscillation portion 104, a voltage detecting portion 108 for outputting a corresponding power source detecting signal by detecting a voltage supplied from a battery portion 109, an element switching portion 107 for controlling to switch a constituent element of the resonance starting oscillation portion 104 to output the start signal by a period in correspondence with the power source detecting signal from the voltage detecting portion 108, and the battery portion 109 for supplying power source to respective constituent elements (the heart beat signal detecting portion 101 through the voltage detecting portion 108) of the transmitter for the heart beat meter.

Here, the heart beat signal detecting portion 101 and the heart beat signal amplifying portion 102 constitute biometric signal detecting means for detecting the biometric signal, the heart beat signal transmission control portion 103, the resonance starting oscillation portion 104 and the element switching portion 107 constitute controlling means, the battery portion 109 constitutes power source means, the voltage detecting portion 108 constitutes power source detecting means. Further, the resonance starting portion 105 and the antenna resonance portion 106 are provided with a function as self-excited oscillation means and constitutes outputting means by generating a biometric information signal of a type of a burst signal in correspondence with the heart beat signal by carrying out the self-excited oscillation operation in response to the start signal from the resonance starting oscillation portion 104 to transmit to a biometric information receiver (receiver for a heart beat meter in the case of the hear beat meter) by wireless (for example, electromagnetic induction).

Further, it is not necessarily needed that the power source is a battery from a view point of restraining a communication distance from being shortened when the power source voltage is reduced. Further, there may be constructed a constitution of supplying power from the battery portion 109 at least to the outputting means and power is supplied to other constituent element from a separate power source and it is not necessarily needed to construct a constitution to supply power from the power source portion 109 to all of the constituent elements.

The transmitter for the heart beat meter is provided integrally with the chest belt (not illustrated), and the heart beat signal detecting portion 101 is used by being mounted to the chest of the measured person to be brought into direct contact therewith by the chest belt. Further, the wrist of the measured person is mounted with a receiver of the heart beat meter (not illustrated) having a function of a wristwatch, receiving biometric information from the transmitter for the heart beat meter and displaying corresponding biometric information or the like.

Figure 2:
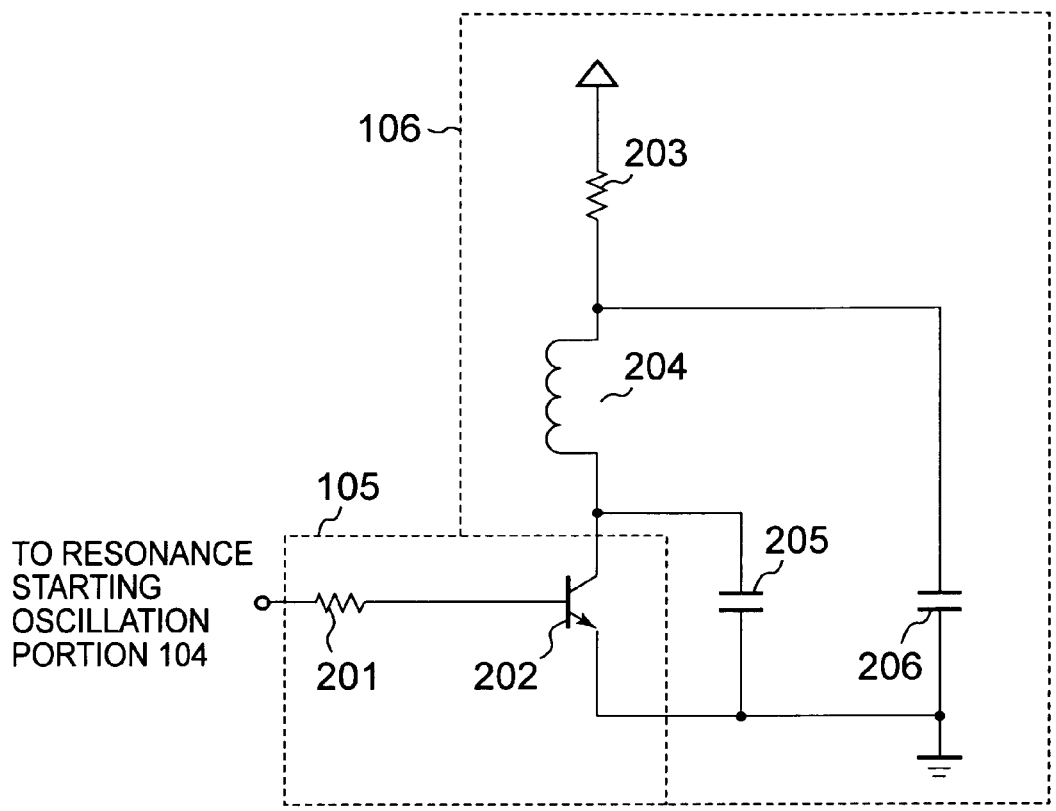
FIG. 2 shows a circuit portion of a constituent element according to the first embodiment of the invention.

FIG. 2 illustrates a circuit portion showing details of the resonance starting portion 105 and the antenna resonance portion 106 in FIG. 1. In FIG. 2, the resonance starting portion 105 includes a resistor 201 and a transistor 202. Further, the antenna resonance portion 106 includes a resistor 203, an antenna coil 204, capacitors 205, 206. A self-excited oscillation circuit is constituted by the resonance starting portion 105 and the antenna resonance portion 106.

Figure 3:
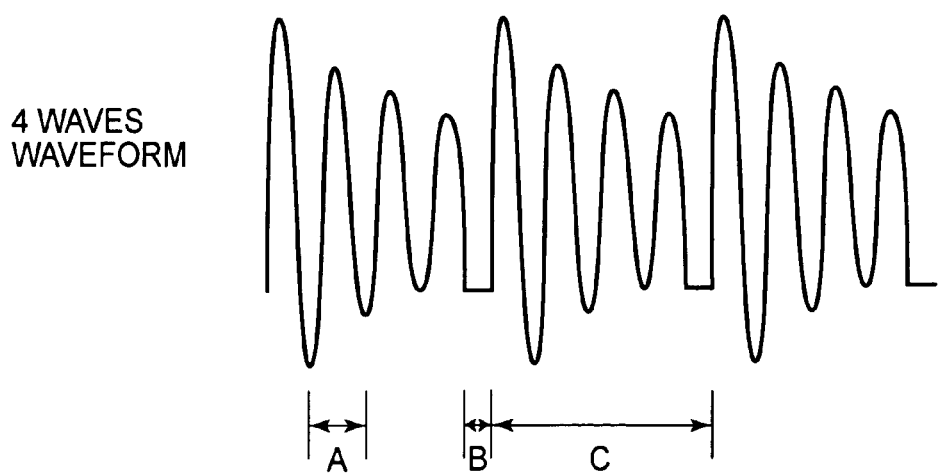
FIG. 3 is a diagram showing a waveform of a biometric information signal transmitted from the biometric information transmitter according to the first embodiment.
Figure 4:
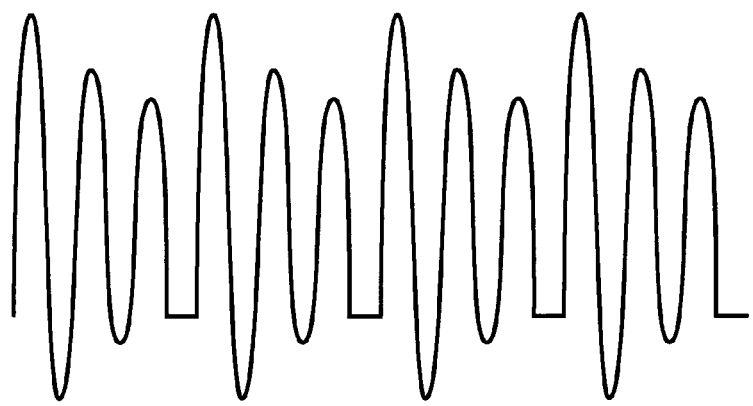
FIG. 4 is a diagram showing a waveform of a biometric information signal transmitted from the biometric information transmitter according to the first embodiment.
Figure 5:
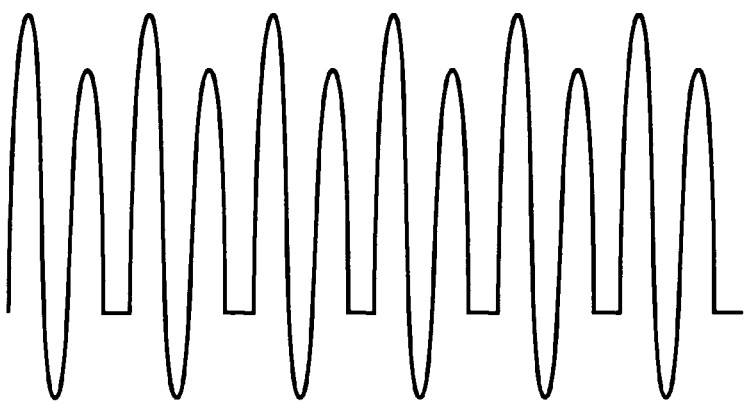
FIG. 5 is a diagram showing a waveform of a biometric information signal transmitted from the biometric information transmitter according to the first embodiment.

FIG. 3 through FIG. 5 are waveform diagrams showing a portion of the biometric information signal transmitted from the biometric information transmitter according to the first embodiment showing a behavior of changing a waveform of the biometric information signal respectively to 4 wave period, 3 wave period, 2 wave period by successively shortening a period of the start signal for starting the resonance starting portion 105.

In FIG. 3, notation A designates a carrier wave, notation B designates a pulse width of the start signal outputted from the resonance starting oscillation portion 104 to the resonance starting portion 105 for starting the resonance starting portion 105, further notation C designates a period of the start signal. These are designated by using the same notations also in FIG. 6 mentioned later.

A transmission output from the antenna resonance portion 106 is increased in an order of 4 wave period, 3 wave period, 2 wave period. The period of the start signal is changed in an order of 4 wave period, 3 wave period, 2 wave period in accordance with a reduction in the voltage supplied from the battery portion 109 although details thereof will be described later.

Figure 6:
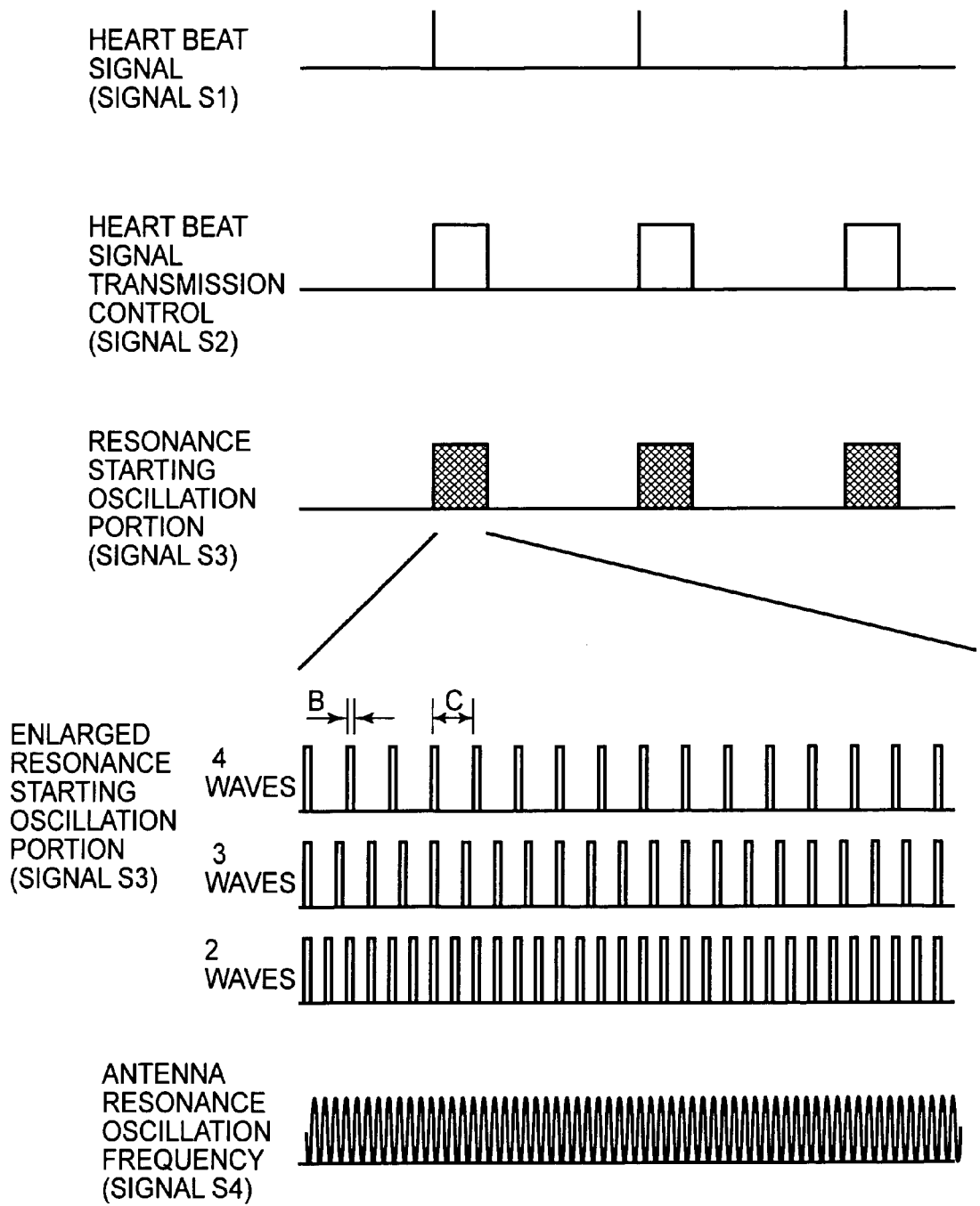
FIG. 6 is a timing output power diagram for explaining operation of the biometric information transmitter according to the first embodiment.

FIG. 6 is a timing output power diagram for explaining operation of the biometric information transmitter according to the first embodiment.

Figure 7:
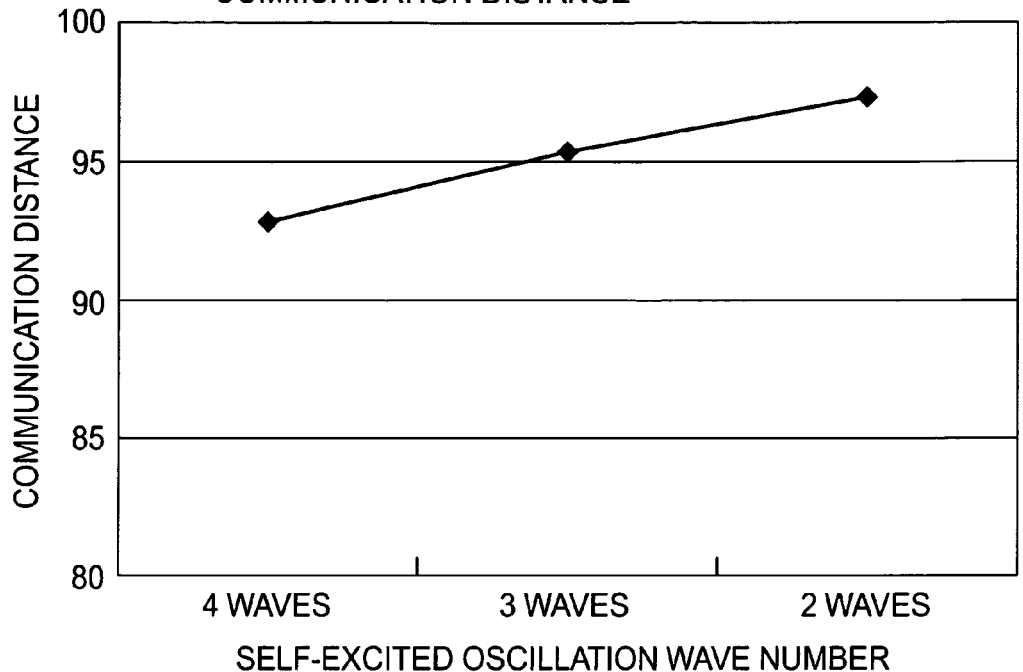
FIG. 7 is a characteristic diagram for explaining the operation of the biometric information transmitter according to the first embodiment.
Figure 8:
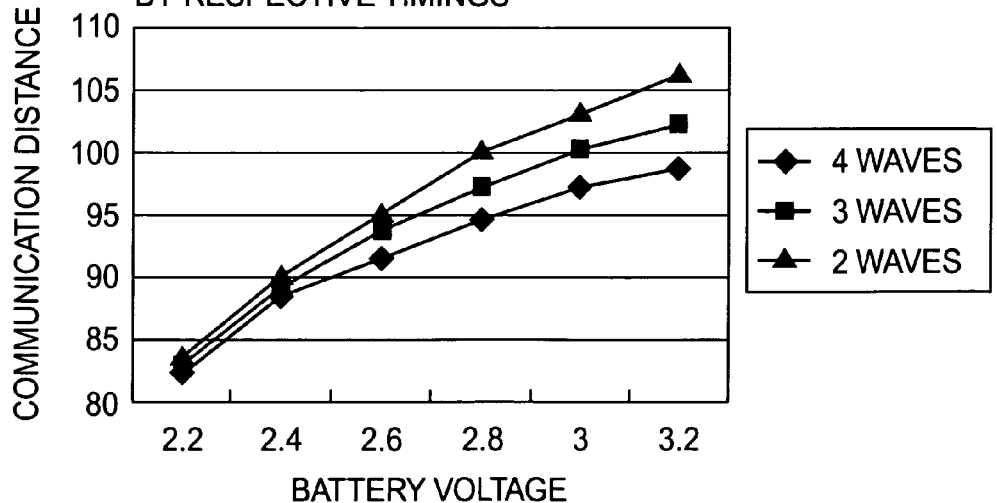
FIG. 8 is a characteristic diagram for explaining the operation of the biometric information transmitter according to the first embodiment.
Figure 9:
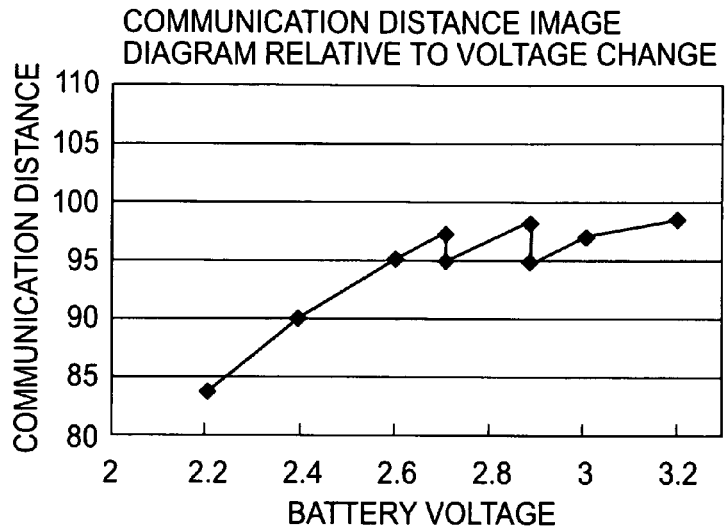
FIG. 9 is a characteristic diagram for explaining the operation of the biometric information transmitter according to the first embodiment.

FIG. 7 through FIG. 9 are characteristic diagrams for explaining operation of the first embodiment.

A detailed explanation will be given of the operation of the first embodiment in reference to FIG. 1 through FIG. 9 as follows.

The heart beat signal detecting portion 101 detects a heart beat from the physical body and outputs a heart beat signal S1 (refer to FIG. 1, FIG. 6). The heart beat signal amplifying portion 102 amplifies the heart beat signal S1 detected by the heart beat signal detecting portion 101 and outputs the amplified heart beat signal to the heart beat signal transmission control portion 103.

The heart beat signal transmission control portion 103 outputs a control signal S2 to the resonance starting oscillation portion 104 and the resonance starting portion 105 in synchronism with the heart beat signal S1 received from the heart beat signal amplifying portion 102, controls the resonance starting oscillation portion 104 to output a start signal S3 in synchronism with the heart beat signal S1, and controls the resonance starting portion 105 to output a biometric information signal in response to the start signal S3.

On the other hand, the voltage detecting portion 108 detects the power source voltage supplied from the battery portion 109 and outputs a power source detecting signal representing the power source voltage. The element switching portion 107 outputs a starting control signal to the resonance starting oscillation portion 104 in response to the power source detecting signal such that a period of the start signal S3 outputted by the resonance starting oscillation portion 104 is set to a value in correspondence with the power source detecting signal.

The resonance starting oscillation portion 104 outputs the start signal S3 by the period in correspondence with the starting control signal from the element switching portion 107 in response to the control signal S2 received from the heart beat signal transmission control portion 103. The start signal S3 is a signal in which the lower the voltage supplied from the battery portion 109, the shorter the period.

The resonance starting portion 105 and the antenna resonance portion 106 carry out the self-excited oscillation operation in response to each start signal S3 and transmit a burst signal in correspondence with the biometric signal S1 to the receiver for the heart beat meter as a biometric information signal S4. Thereby, the biometric information signal S4 is outputted during a time period of generating the signal S2.

Explaining operation of transmitting the biometric information signal S4 further in details, the resonance starting portion 105 and the antenna resonance portion 106 start the self-excited oscillation operation in response to the start signal S3 to output as the biometric information signal S4, at this occasion, the resonance starting oscillation portion 104 outputs a plurality of kinds (3 kinds according to the embodiment) of the start signals S3 having different periods in response to the start control signal from the element switching portion 107.

That is, the voltage detecting portion 108 outputs a plurality of kinds (3 kinds according to the embodiment) of the power source detecting signal in accordance with a level of the power source voltage supplied from the battery portion 109. The element switching portion 107 outputs the start control signal of the kind in correspondence with the power source detecting signal to the resonance starting oscillation portion 104 and controls the resonance starting oscillation portion 104 to generate the start signal S3 of the period in accordance with the power source detecting signal from the voltage detecting portion 108. The resonance starting oscillation portion 104 outputs the start signal S3 of the period in correspondence with the starting control signal from the element switching portion 107 to the resonance starting portion 105.

The resonance starting portion 105 starts the self-excited oscillation operation along with the antenna resonance portion 106 in response to the respective start signals S3 and transmits the biometric information signal S4 to the receiver for the heart beat meter. According to the start signal S3, when the power source voltage exceeds a first predetermined voltage, a period thereof is set to a maximum first period (according to the embodiment, a period of 4 waves of the biometric information signal S4 (refer to FIG. 3)), when the power source voltage is equal to or smaller than the first predetermined voltage and equal to or larger than a second predetermined voltage, the period is set to a second period (according to the embodiment, a period of 3 waves of the biometric information signal S4 (refer to FIG. 4)) smaller than the first period, when the power source voltage is less than the second predetermined voltage, the period is set to a third period (according to the embodiment, a period of 2 waves of the biometric information signal S4 (refer to FIG. 5)) smaller than the second period.

FIG. 7 is a diagram showing a relationship between a resonance frequency of the self-excited oscillation circuit and a communication distance. As shown by FIG. 7, according to the communication distance, since a transmission output is increased in an order of 4 waves period, 3 waves period, 2 waves period, the communication distance is prolonged in accordance therewith.

FIG. 8 is a diagram showing a relationship between the voltage supplied from the battery portion 109 and the communication distance. As shown by FIG. 8, the lower the voltage supplied from the battery portion 109, the shorter the communication distance. Further, since the transmission output is reduced in an order of 2 waves period, 3 waves period, 4 waves period and therefore, the communication distance is shortened in accordance therewith.

FIG. 9 is a diagram showing a behavior of changing the period of the start signal S3 in accordance with a variation in the voltage supplied from the battery portion 109. According to the example of FIG. 9, there is shown an example of driving by 2 waves period when the voltage supplied from the battery portion 109 is equal to or lower than 2.7V, 3 waves period when the supply voltage is between 2.7V through 2.9V, 4 waves period when the supply voltage is equal to or higher than 2.9V.

By driving in this way, even when the power source voltage is lowered, the communicatable distance can be restrained from being shortened. Further, a variation in the communicatable distance can be restrained. Further, by automatically changing a period of starting the self-excited oscillation from a value of the power source voltage, the stable communication distance can be provided even when the power source voltage is lowered without making a user conscious thereof.

Figure 10:
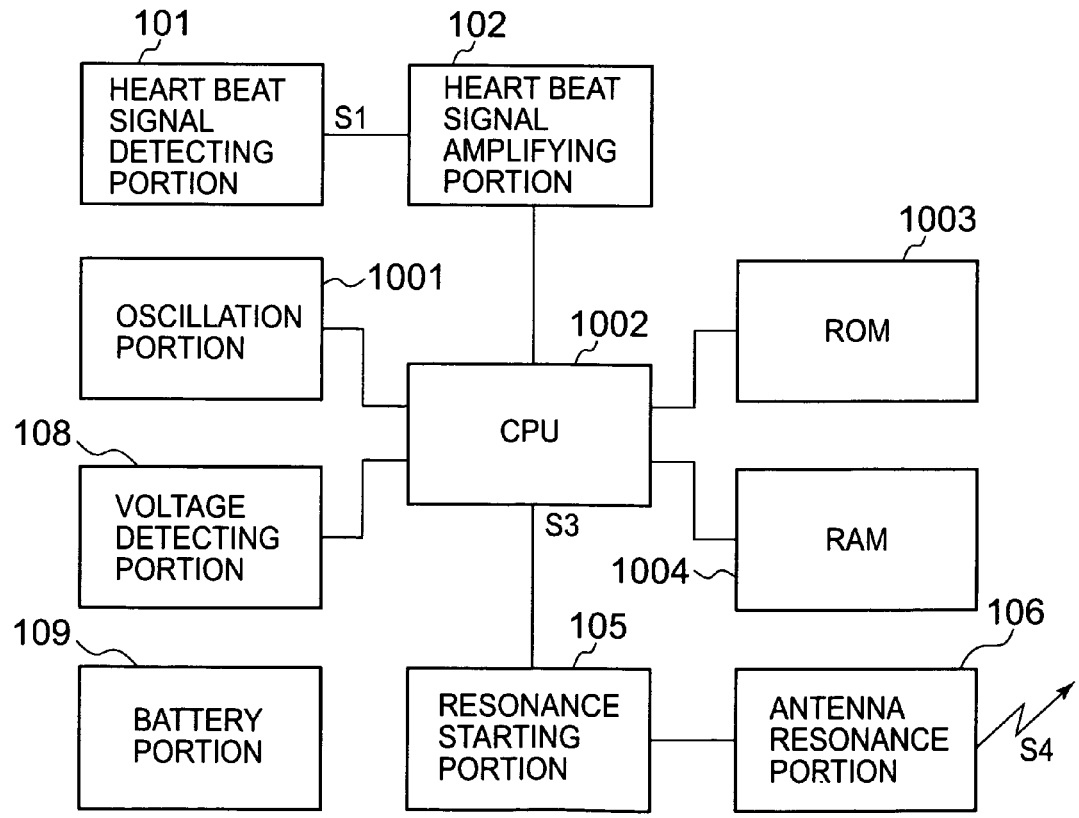
FIG. 10 is a block diagram of a biometric information transmitter according to a second embodiment of the invention.

FIG. 10 is a block diagram of a biometric information transmitter according to a second embodiment of the invention showing an example of a transmitter for a heart beat meter. Although the first embodiment is constituted by a hardware, according to the second embodiment, functions of the heart beat signal transmission control portion 103, the resonance starting oscillation portion 104 and the element switching portion 107 are constituted to be realized by a central processing unit (CPU). Further, in FIG. 10, portions the same as those of FIG. 1 are attached with the same notations.

In FIG. 10, a transmitter for a heart beat meter includes the heart beat signal detecting portion 101 for detecting to output the heart beat signal of the measured person, the heart beat signal amplifying portion 102 for amplifying to output the heart beat signal from the heart beat signal detecting portion 101, the resonance starting portion 105 and the antenna resonance portion 106 for carrying out the self-excited oscillation operation in response to the start signal, the voltage detecting portion 108 for detecting the voltage supplied from the battery portion 109 and outputting the corresponding power source detecting signal, the battery portion 109 for supplying the power source to respective constituent elements of the transmitter for the heart beat meter, an oscillation portion 1001 for generating a signal of a predetermined frequency of a clock signal or the like, a central processing unit (CPU) 1002 for outputting the start signal and carrying out various controls, a read only memory (ROM) 1003 for storing a program executed by CPU 1002, a random access memory (RAM) 1004 for storing data of the period of the start signal, the heart beat data or the like.

Here, the heart beat signal detecting portion 101 and the heart beat signal amplifying portion 102 constitute the biometric signal detecting means for detecting the biometric signal, the battery portion 109 constitutes the power source means, the voltage detecting portion 108 constitutes the power source detecting means, CPU 1002 constitutes controlling means, ROM 1003 and RAM 1004 constitute storing means. Further, the resonance starting portion 105 and the antenna resonance portion 106 function as self-excited oscillation means for carrying out self-excited oscillation operation in response to the start signal from CPU 1002 and constitutes outputting means for outputting the biometric information signal to the receiver.

Further, similar to the first embodiment, it is not necessarily needed that the power source is a battery, further, it is not necessary to supply power to all of the constituent elements from the battery portion 109, but power may be constituted to be supplied to at least the outputting means. Further, the transmitter for the heart beat meter is integrally provided with the chest belt (not illustrated), and the heart beat signal detecting portion 101 is used by being mounted to be brought into direct contact with the chest of the measured person by the chest belt. The wrist of the measured person is mounted with the receiver for the heart beat meter (not illustrated).

Figure 11:
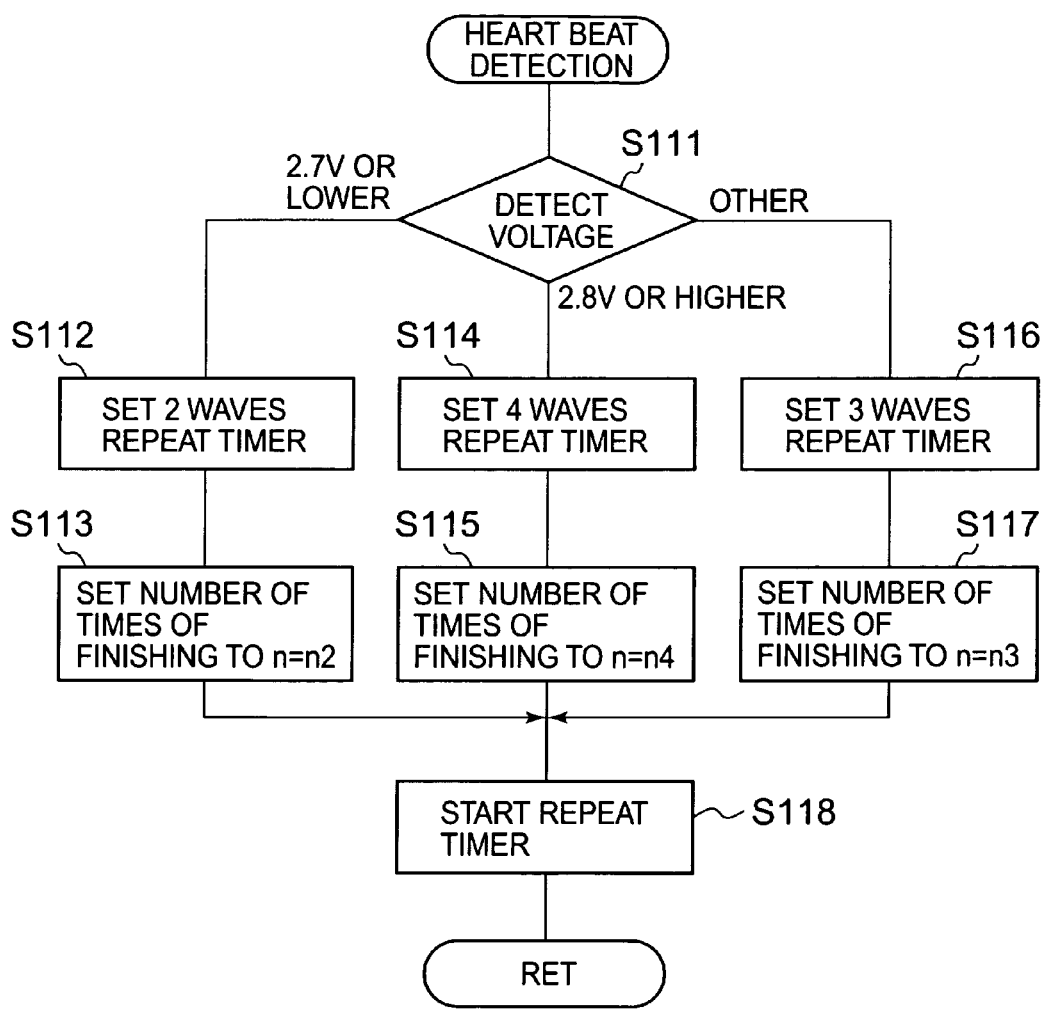
FIG. 11 is a flowchart showing processings of the biometric information transmitter according to the second embodiment of the invention.
Figure 12:
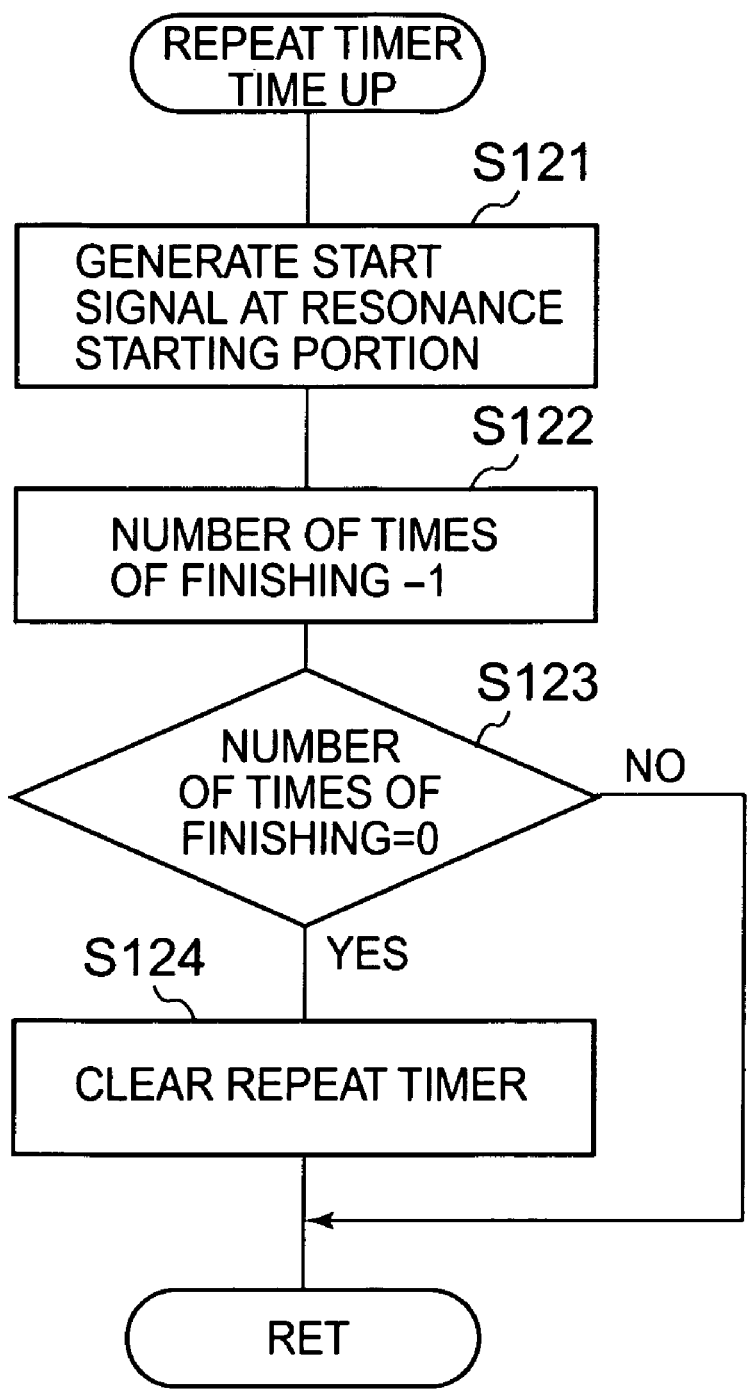
FIG. 12 is a flowchart showing processings of the biometric information transmitter according to the second embodiment of the invention.

FIG. 11 and FIG. 12 are flowcharts showing operation of the transmitter according to the second embodiment, mainly showing processings carried out by executing the program stored to ROM 1003 by CPU 1002.

Operation of the second embodiment will be explained in reference to FIG. 10 through FIG. 12 as follows. Further, the explanation will be given by omitting a portion of the operation duplicated with the operation of the first embodiment.

The heart beat signal detecting portion 101 detects to output the heart beat signal S1 provided from the physical body. The heart beat signal amplifying portion 102 amplifies the heart beat signal S1 detected by the heart beat signal detecting portion 101 to output to CPU 1002.

When CPU 1002 receives the heart beat signal S1, CPU 1002 determines the voltage value supplied from the battery portion 109 based on the power source signal from the voltage detecting portion 108 representing the voltage supplied from the battery portion 109 (step S111 of FIG. 11).

When CPU 1002 determines that the voltage supplied from the battery portion 109 is equal to or lower than 2.7V, CPU 1002 sets the period of the start signal S3 to 2 waves period by setting a 2 waves repeat timer (step S112), sets a number of times of finishing the start signal S3 (number of times of outputting start signal) to a predetermined value (for example, 31) (step S113) thereafter, starts a repeat timer (S118).

At step S111, when CPU 1002 determines that the voltage supplied from the battery portion 109 is equal to or higher than 2.8V, CPU 1002 sets a 4 wave repeat timer, sets the period of the start signal S3 to 4 waves period (step S114), sets a number of times of finishing the start signal S3 (number of times of outputting start signal) to a predetermined value (for example, sets to 16 such that a number of waves of the biometric information signal is to a degree the same as that of a number of waves set by S113) (step S115) thereafter, starts the repeat timer (step S118).

Further, at step S111, when CPU 1002 determines that the voltage supplied from the battery portion 109 is a voltage between 2.7V and 2.8V, CPU 1002 sets a 3 wave repeat timer, sets a period of the start signal S3 to 3 waves period (step S116), sets a number of times of finishing the start signal S3 (number of times of outputting start signal) to a predetermined value (for example, set to 21 such that a number of waves of the biometric information signal is to a degree the same as those of the numbers of waves set at steps S113, S115) (step s117) thereafter, starts the repeat timer (step S118).

Next, when the repeat timer started at the step S118 finish time after a predetermined time period, CPU 1002 outputs the start signal S3 to the resonance starting portion 105 (step S121 of FIG. 12). The resonance starting portion 105 and the antenna resonance portion 106 carry out the self-excited oscillation operation in response to the start signal S3 and transmit a burst signal in correspondence with the biometric signal S1 to the receiver for the transmitter as the biometric information signal S4.

Next, CPU 1002 subtracts 1 from the set number of times of finishing (step S122), when the remaining number of times of finishing is 0 (step S123), CPU 1002 returns to the initial processing after clearing the repeat timer (step S124), when the remaining number of times of finishing is not 0, CPU 1002 immediately returns to the initial processing.

Thereafter, by repeating the processings, similar to the first embodiment, the start signal S3 having a plurality of periods (according to the embodiment, 2 waves period through 4 waves period) in accordance with the voltage supplied from the battery portion 109 is outputted from CPU 1002, and the biometric information signal having power in accordance with the period of the start signal is transmitted from the antenna resonance portion 106.

Therefore, also by the second embodiment, the communicatable distance can be restrained from being shortened even when the power source voltage is lowered. Further, the variation in the communicatable distance can be restrained. Further, there is achieved an effect of capable of providing the stable communication distance even when the power source voltage is lowered by automatically changing the period of starting the self-excited oscillation from the value of the power source voltage without making the user conscious thereof.

Further, although an explanation has been given by taking an example of detecting heart beat according to the embodiments, the invention is not limited thereto but is preferable for measuring a biometric signal generated periodically. For example, the invention may be constituted to detect pulse or number of steps other than heart beat.

According to the invention, a communicatable distance can be restrained from being shortened even when the power source voltage is lowered.

The invention is applicable to the biometric information transmitter for detecting to transmit the biometric signal of heart beat, pulse, number of steps or the like of a person of not only the heart beat meter but also a pulsimeter, a walk number meter or the like.

What is claimed is:

1. A biometric information transmitter comprising:
   biometric signal detecting means for detecting a biometric signal;
   outputting means for outputting a biometric information signal in correspondence with the biometric signal detected by the biometric signal detecting means, the outputting means including self-excited oscillation means for generating the biometric information signal in correspondence with the biometric signal;

power source means for supplying a drive power to at least the outputting means;

power source detecting means for detecting a voltage of the power source means and outputting a corresponding power source detecting signal; and controlling means for controlling the transmission output of the outputting means by controlling a drive timing output power of the self-excited oscillation means in accordance with the power source detecting signal from the power source detecting means.

2. A biometric information transmitter according to claim 1; wherein the controlling means controls the transmission output of the outputting means by controlling an output power of the self-excited oscillation means in accordance with the power source detecting signal from the power source detecting means.

3. A biometric information transmitter according to claim 1; wherein the controlling means shortens a period of driving the self-excited oscillation means to a predetermined value when the power source voltage supplied from the power source means to the outputting means is equal to or lower than a predetermined voltage.

4. A biometric information transmitter according to claim 1; wherein the controlling means comprises a central processing unit that executes a program stored in a storing means.

5. A biometric information transmitter according to claim 1; wherein the biometric signal detecting means detects heart beat, pulse or a number of steps as the biometric signal; and wherein the controlling means controls the outputting means to output the biometric information at every time of detecting the biometric signal by the biometric signal detecting means.

* * * * *